United States Patent [19]
Magnusson et al.

[11] Patent Number: 5,401,399
[45] Date of Patent: Mar. 28, 1995

[54] WATER PURIFICATION SYSTEM

[76] Inventors: Jan H. Magnusson; Kristofer J. Magnusson, both of 117 Wild Wood Beach Rd., Mahtomedi, Minn. 55115

[21] Appl. No.: 113,713

[22] Filed: Aug. 27, 1993

[51] Int. Cl.⁶ .............................................. C02F 9/00
[52] U.S. Cl. ................................... 210/136; 210/199; 210/202; 210/206; 210/266; 210/282; 210/284
[58] Field of Search ............... 210/764, 136, 199, 259, 210/266, 282, 283, 284, 202, 206

[56] References Cited
U.S. PATENT DOCUMENTS

| | | | |
|---|---|---|---|
| 3,056,502 | 10/1962 | Zwicky | 210/283 |
| 4,238,477 | 12/1980 | Lambert et al. | 424/79 |
| 4,383,920 | 5/1983 | Muller et al. | 210/284 |
| 5,126,044 | 6/1992 | Magnusson et al. | 210/282 |

*Primary Examiner*—Ivars Cintins
*Attorney, Agent, or Firm*—Douglas L. Tschida

[57] ABSTRACT

A multi-section manifold system containing a number of replaceable filter and purification cartridges for treating the water supply of medical and dental facilities. The system operates to introduce increased concentrations of a preferred bactericide to the water immediately adjacent patient dispensing appliances. Control valving regulates and segregates flow through separate cartridges at the manifolds. A first manifold removes coarse particulates and sediment and exposes the water to an initial bactericide. A second manifold removes finer contaminants. A third concentrator manifold contains a bactericide cartridge having a percolation chamber which enhances the iodine concentration of the water in the range of 3 to 10 ppm at the patient dispensing apparatus. The percolation cartridge includes proximal and distal bactericide chambers which are, separated by an intermediate reservoir or percolation chamber.

10 Claims, 4 Drawing Sheets

WATER PURIFICATION SYSTEM

BACKGROUND OF THE INVENTION

The present invention relates to water treatment systems and, in particular, to a manifold system wherein a number of manifold sections separately contain preferred, replaceable treatment cartridges. Associated conduits and control valving monitor and appropriately regulate flow through the system to provide water having an accentuated concentration of a preferred bactericide.

As scientists have become more aware of the many ways in which diseases, microorganisms (e.g. bacteria, parasites and viruses) and volatile organic contaminants (VOC's) are communicated, efforts have been extended to improve or to develop water treatment facilities to reduce the transfer of such contaminants. Many user environments which have previously received relatively little attention are now being studied.

An impetus of the recent attention was a widely reported case of AIDS which spread to patients of a dental facility. Another disease of concern is legionnaires disease, which is believed to be spread in high moisture environments such as found in dental treatment facilities.

Two user environments which have been the focus of much recent attention are dental and medical facilities. Both of these latter facilities are exposed on a daily basis to unusually large varieties of microorganisms which can effect the health of the general population. The artificially high incidence and frequency of the exposure of either facility requires added precautions to properly deal with communicable diseases.

Depending upon the size of the facility, such as hospitals and larger medical and dental clinics, a limited filtration and treatment capability may already exist to condition the facility's general water supply. Any available system, however, is typically concerned only with treating the water that is received from the service utility or well to remove selected contaminants, sediments and particulates and to prevent blockage of the distribution system.

The institution may also occasionally take steps to back-flush or treat the plumbing or water distribution system to decontaminate the plumbing conduits and fixtures. These attempts are intended to decontaminate the general distribution system of contaminants which have accumulated and possibly multiplied over time, upon being admitted from the water source. These efforts typically require shutting the system down for a period of time, after chemical treatments are added; allowing the chemicals time to act; and purging or back-flushing the system of the treatment chemicals.

Although contaminants may enter a distribution system from the water utility or well, it has been discovered that contaminants and microorganisms are equally likely to migrate into the system from water dispensing fixtures in contact with the patient. Over time and with the accumulation of the contaminants and the multiplication of the collected microorganisms, the contaminants can be dispensed to subsequent users of the dispensing equipment.

Water fountains and patient treatment stations, such as used in dental offices, are particularly susceptible to the foregoing problems. The users of these devices are intimately exposed to transmit and receive microorganisms and contaminants from and to the distribution system through physical contact with the dispensing equipment. The degree and duration of the contact is greater for dental stations where water is dispensed via a provided glass, which permits patient rinsing; a high pressure spray, which is dispensed from the drill; and a low pressure sprayer, which permits the dentist to direct a low volume flow for cleaning. Dental stations also exhibit a suction effect with the operation of the drill which enhances the potential of reverse migration of microorganisms from each patient.

Attempts have not been made to provide systems or equipment for continuously treating the water at such fixtures.

Appreciating the potential for bacteria, parasites and viruses to migrate back into the conduits of the dispensing system, studies have been conducted at various institutions to objectively monitor the significance of the problem. One such study has been conducted by Jan Carlsson at the Umea University, Umea, Sweden. This study has measured significant initial concentrations of bacteria along with significant growth and regrowth of bacteria on a daily basis at a number of dental test stations. This study has also monitored the effects of equipment intended to provide solutions to the problem.

Upon particularly incorporating the system of the present invention at ones of such stations, appreciable reductions in the concentration of bacteria has been demonstrated. In fact the total elimination of bacteria has been demonstrated over a single day of use. Such studies have further confirmed the necessity of ongoing water purification treatments and preferably a mechanism for controllably or continuously dispensing bactericides and in close proximity to the dispensing equipment to assure the availability of disease and contaminant free water.

SUMMARY OF THE INVENTION

It is accordingly a primary object of the present invention to provide a system for treating water and liquids dispensed from equipment and fixtures exhibiting a potential for reverse migration of bacteria into a water distribution system.

It is a further object of the invention to provide apparatus compatible with dental and medical facilities and which may be mounted in close proximity to patient treatment stations.

It is a further object of the invention to provide apparatus capable of maintaining and dispensing an increased concentration of one or more preferred bactericides in close proximity to each treatment station.

It is a further object of the invention to provide a system which is compatible with replaceable treatment cartridges and thereby accommodate a variety of user settings and water conditions.

It is a further object of the invention to provide a system including a number of manifolds which separately contain cartridges designed to remove sediment, suspended particulates, microorganisms (i.e. bacteria, parasites, viruses) and VOC's from the liquid.

It is a further object of the invention to provide a system including control valving for segregating one or more of the manifolds and treatment cartridges from the system.

It is a further object of the invention to provide at least one manifold which dispenses a controlled, and predetermined relatively large concentration of one or more preferred bactericides into the system.

It is a still further object of the invention to provide a replaceable cartridge having proximal and distal chambers which contain a multi-valent, iodine based resin bactericide, and which chambers are separated by an intermediate percolation reservoir or void.

Various of the foregoing objects, advantages and distinctions of the invention are obtained in a presently preferred, multi-section manifold system. The system includes a novel cartridge which contains a percolation reservoir or void intermediate proximal and distal bactericide dispensing chambers. The percolation cartridge is contained in a concentrator manifold that is mounted in close proximity to a patient treatment station. The concentrator manifold is configured to provide relatively high concentrations of a multi-valent iodine resin bactericide to the water, particularly in the range of 3 to 10 ppm of iodine. The enhanced levels of bactericide serves to continuously devitalize the intermediate distribution conduits and dispensing fixture during use and in-between uses. The bacteria concentration can be varied by varying the bactericide types and concentrations and the size of the percolation reservoir. Separate and extraneous cleanings are thereby avoided.

Also provided with the system are a pair of manifolds which support separate cartridges for maintaining an ambient water condition in relation to the source supply. Depending upon the condition of the water supply, the cartridges remove suspended sediment, particulates and other contaminants.

Associated distribution conduits, a flow meter and valving maintain a preferred water condition. A pair of two-way valves and a check valve mounted to the inlet and outlet sides of the concentrator manifold permit the selective coupling and decoupling of the concentrator manifold from the treatment system. Decoupling is desired where a patient may be allergic to the bactericide.

Still other objects, advantages and distinctions of the invention will become more apparent from the following detailed description which is presented with respect to the appended drawings. To the extent various modifications and improvements have been considered, they are described as appropriate. The invention should not be interpreted in strict limitation to the disclosed embodiment. Rather, the invention should be interpreted within the full scope of the appended claims.

DESCRIPTION OF THE PREFERRED EMBODIMENT

Figure 1:
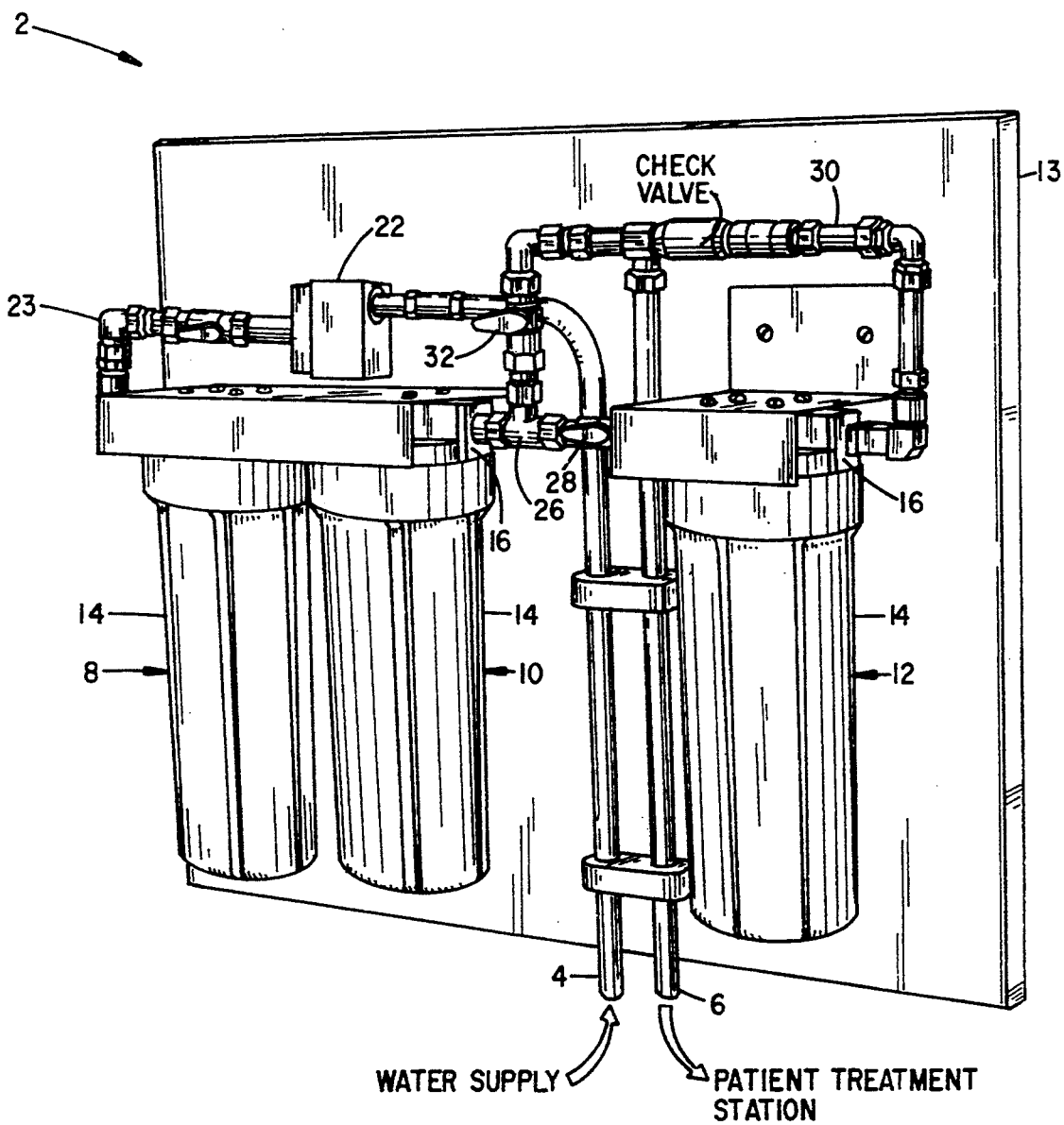
FIG. 1 is a perspective drawing of the manifold purification system of the invention.

Referring to FIG. 1, a perspective drawing is shown of a manifold purification system 2 of the invention. The system 2 finds particular application in dental and medical offices for treating and purifying water which is dispensed at patient treatment stations distributed about the premises. Depending upon the application and the water requirements of the station (e.g. 300 cc per patient over a twenty-five minute treatment period), the system 2 has adequate throughput capacity to accommodate from five to ten patient stations.

As presently constructed, the system 2 provides a purification capacity between cartridge replacements of 6400 liters and accommodates a throughput flow rate of 2 liters per minute, presuming the use of new cartridges. The system 2 is organized to treat water which is provided from a utility source that is coupled to a conduit 4 to remove suspended sediment, particulates, contaminant microorganisms (e.g. bacteria-*E. coli b*, *vibrio cholera*, *S. aureus*, *S. pyogenes*, *S. schottmulleri* and *L. pneumophila*; parasites—giardiaasis, *G. muris* cysts, and cryptosporidiosis; and viruses-polio type 1, herpes simplex 2, coxsacle and echo type 2) and VOC's.

The system 2 also produces treated water at the outlet conduit 6 having an iodine concentration in the range of 3 to 10 ppm. Such a concentration is sufficient to purify the conduits intermediate the system manifolds and the patient station of typical contaminant and microorganism migration and growth which can occur within the conduits and/or at the patient station.

Figure 2:
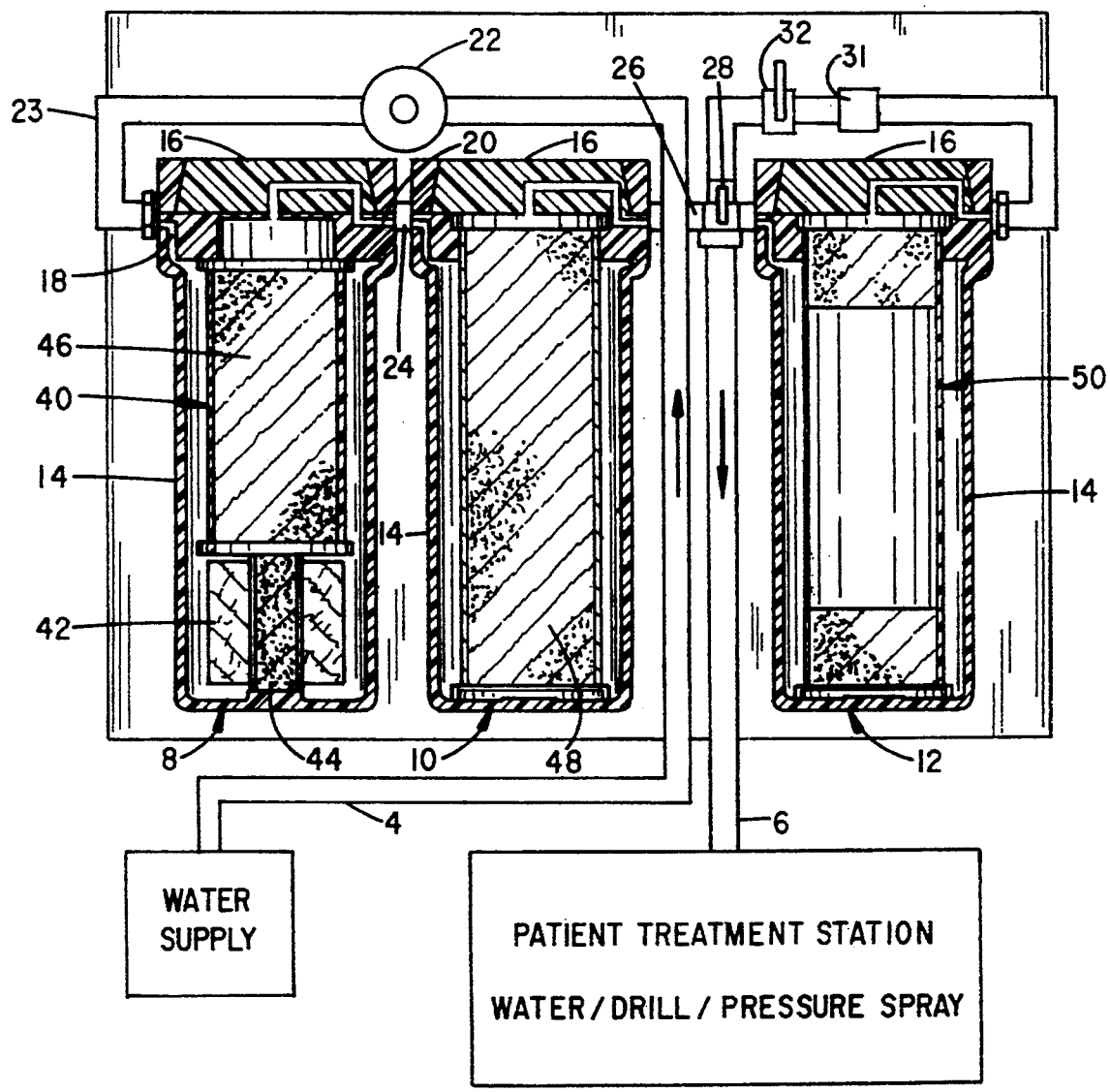
FIG. 2 is a diagrammatic drawing of the purification system shown in cutaway.

The system 2 includes three separate manifold assemblies 8, 10 and 12, each of which contain a replaceable purification cartridge that is selected to treat the water in a preferred manner (reference FIG. 2). Each of the manifold assemblies 8, 10 and 12 is mounted to a mounting panel 13 and includes a threaded housing 14 which depends from a headpiece 16. Each housing 14 is secured to a headpiece 16 via mating threads (not shown). Presently the manifolds 8, 10 and 12 are selected to be identical, although the size and type could be varied depending upon the requirements to properly treat the distribution system.

With attention also directed to FIG. 2, liquid is directed from an inlet port 18 at each headpiece 16 to the interior of the housing 14 and through a contained cartridge to an outlet port 20 which is coupled to the inlet port 18 of the adjacent manifold assembly. The inlet port 18 of the manifold assembly 8 is connected to the inlet conduit 4 via an intermediate system shutoff valve 22 and conduit 23. The valve 22 preferably includes a flow meter to monitor system use over time.

The outlet port 20 of the manifold 8 is coupled to the inlet port of the manifold 10 via a coupler 24. The outlet port 20 of the manifold 10 is serially coupled to the inlet port 18 of the assemblies 12 via a coupler 26 and a two-way control valve 28. The outlet port 20 of the manifold 12 is coupled via a conduit 30 to a check valve 31 and a second two-way control valve 32 which is separately coupled to the outlet conduit 6.

With the appropriate setting of the control valves 28 and 32, the treated liquids from the manifolds 8 and 10 can be directed to bypass the concentrator manifold assembly 12. The ability to bypass the concentrator manifold 12 is particularly desirable for patients who may exhibit allergic reactions to the bactericide (i.e. a multi-valent iodine). For such patient's, the flow valve 28 is closed to prevent flow to the manifold 12, while the valve 32 is opened to convey the flow from the manifold 10 to the outlet conduit 6. For normal conditions, the valve 28 is opened and the valve 32 is closed to permit serial flow through the concentrator manifold 12 and to the outlet conduit 6.

With continuing attention to the cross section system diagram of FIG. 2, the manifold assembly 8 includes a replaceable treatment cartridge 40. Such a cartridge is described in U.S. Pat. No. 5,126,044 and is available from Ecomaster Corporation of St. Paul, Minn. The cartridge 40 includes a cast carbon block sediment filter 42 having a nominal porosity of 1.0 microns, which mounts about a bactericide chamber 44 that projects from one end of the cartridge 40. A suitable bactericide is included in the chamber 44. The presently preferred bactericide comprises a multi-valent, iodine based resin material which is commercially available and further described in U.S. Pat. No. 4,238,477.

A second cast carbon filter 46 having a nominal porosity of 0.5 microns is mounted downstream of the bactericide chamber 44 and within the cartridge housing. Admitted liquids are thus sequentially exposed to the carbon based filters 42 and 46 with an intermediate exposure to the bactericide at the chamber 44.

The pre-conditioned water is next conducted through the manifold assembly 10, where additional and finer contaminants are removed in a carbon bed filter. In particular, the housing 14 of the manifold 10 contains a cartridge which contains a solid cast carbon block 48 having a nominal porosity of 0.2 microns to remove and reduce any concentration of VOC's, waterborne chemicals and other smaller contaminants.

Figure 3:
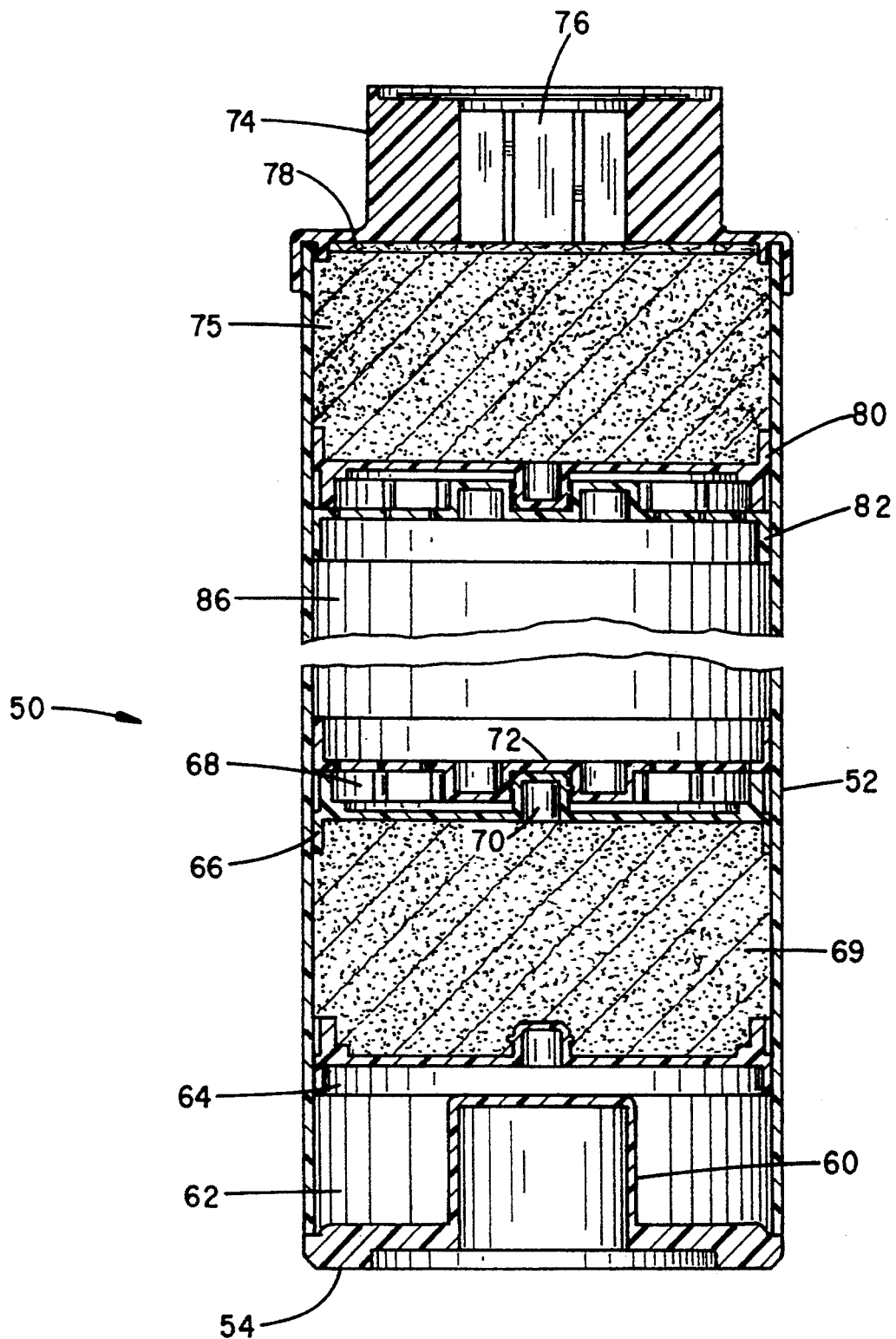
FIG. 3 is a cross section drawing of the reservoir bactericide cartridge contained in the concentrator manifold.
Figure 4:
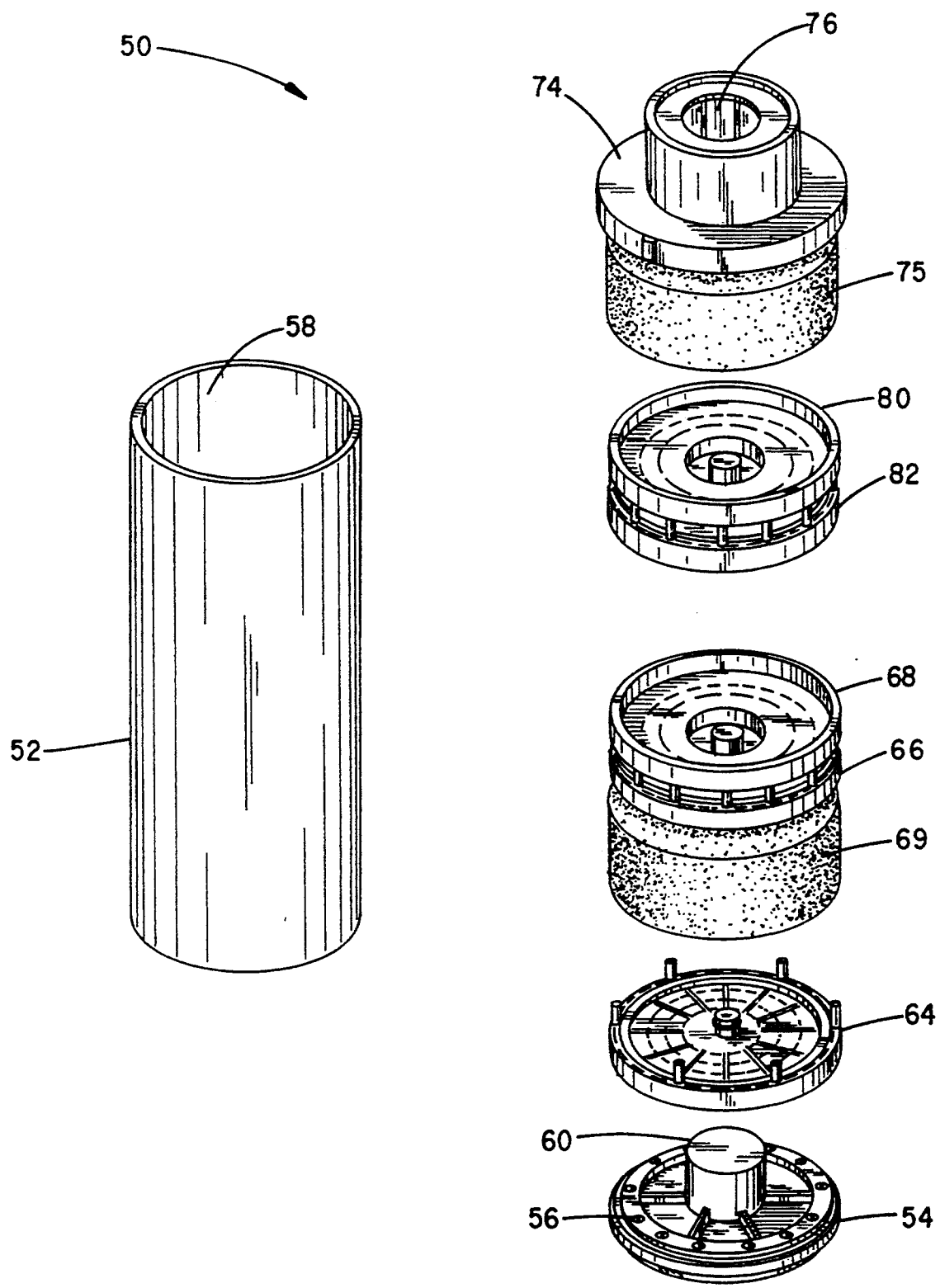
FIG. 4 is an exploded assembly drawing of the reservoir bactericide reservoir cartridge.

Lastly, the pretreated water is conveyed to the concentrator manifold assembly 12 where the bactericide concentration in the water is raised to a concentration in the excess of 3 to 6 ppm. The increased bactericide concentration is achieved with the use of a replaceable cartridge 50 which mounts within the housing 14. A generalized cross section drawing of the cartridge 50 is shown at FIG. 3. FIG. 4, in turn, depicts a detailed exploded assembly drawing of the cartridge 50.

With reference to FIGS. 3 and 4, the cartridge 50 includes a cylindrical plastic housing 52 having a nominal 2.7 inch diameter and 10 inch length. An inlet end cap 54 includes a number of ports 56 which admit liquid received from the housing 14 to the interior 58 of the housing 52. A pedestal 60 projects from the center of the end cap 54 to provide a cavity 62 adjacent a first screen retainer 64. A pair of back-to-back mounted screens 66, 68 are displaced from the screen 64 within the housing a sufficient distance to contain a 50 to 100 cc's of bactericide 69.

The screens 64, 66 and 68 are formed of a polypropylene material and exhibit a number of slots or through apertures to permit the passage of the water while retaining the bactericide. The screens 66, 68 are secured to one another at a mating pedestal 70 and cavity 72.

The distal end of the cartridge 50 includes an end cap 74 having a center bore 76. A porous felt washer 78 mounts to the end cap 74 and adjacent to which a second quantity of bactericide 75 is contained in a second bactericide storage chamber. The size of the second chamber is defined by lower screens 80 and 82. An approximate quantity of 50 to 100 cc's of bactericide is contained in the distal bactericide chamber. The end caps 54 and 74 are sonic welded to the housing 52.

A percolation reservoir or void 86 is formed between the bactericide chambers. As presently constructed, the reservoir 86 accommodates an approximate volume of 500 cc's of liquid. This can be varied depending upon the relative types and concentrations of bactericides at the bactericide chambers. The percolation reservoir 86 permits the accumulation of relatively high concentrations of the bactericide within the contained water. This occurs since the contained water is exposed to the bactericide of the proximal and distal bactericide chambers for relatively long durations, depending upon the treatment flow characteristics. A relatively high concentration bactericide buffer is thus obtained and past which bacteria from the distribution system and patient treatment station is not able to migrate.

As significant, the bactericide concentration is such that during normal liquid draw down and once the treatment system achieves equilibrium, the high concentration of bactericide, upon being admitted to the relatively short length of conduit to the patient station, devitalizes any intermediate bacteria contained in the conduit or liquids. Over time and depending upon the nominal throughput required by the patient treatment station, an equilibrium bactericide concentration in the range of 3 to 10 ppm is preferably developed within the intermediate conduits which devitalizes any bacteria which may migrate or be vacuumed from the patient station into the liquid distribution system.

The residual bactericide from the concentrator manifold 12 is thus available on a continuous basis, not only during patient treatments, but also during periods of non-use to assure a safe and conveniently available supply of purified water.

Although the invention has been described with respect to a presently preferred system organization and cartridges 40, 48 and 50, it is to be appreciated still other organizations may be suggested to those skilled in the art. Similarly, varieties of other bactericides may be contained within the residual cartridge 50 in lieu of the presently preferred iodine based bactericide. The following appended claims should accordingly be interpreted to include all those equivalent embodiments within the spirit and scope thereof.

What is claimed is:

1. A water treatment system comprising:
    a) a plurality of manifolds wherein each manifold includes a disposable treatment cartridge and means for containing each cartridge within each manifold and directing liquid flow through each cartridge, wherein a first of said cartridges comprises a carbon filter, a chamber containing a first bactericide and a second carbon filter, wherein a second of said cartridges comprises a third carbon filter, wherein a third cartridge comprises second and third chambers, which second and third chambers contain second and third bactericides and which second and third chambers are separated by an intermediate open cavity space and wherein said second and third bactericides provide a concentration of 3 to 10 ppm of bactericide to said liquid;
    b) means for coupling an inlet port of one of said manifolds to a water supply;
    c) means for serially coupling each of said manifolds to one another; and
    d) means for coupling an outlet port of one of said manifolds to a patient treatment station, such that said system provides water to said patient treatment station having a bactericide concentration sufficient to maintain distribution conduits intermediate said patient treatment station essentially bacteria and contaminant free.

2. Apparatus as set forth in claim 1 including segregation means for selectively segregating at least one of said manifolds from liquid flow directed through said system.

3. Apparatus as set forth in claim 2 wherein said third cartridge is contained in a concentrator manifold which is mounted in close proximity to the patient station, and wherein said segregation means comprises a first two-way valve coupled intermediate to an inlet port of said concentrator manifold, a check valve coupled to an outlet port of said concentrator manifold and to said patient treatment station, and a second two-way valve coupled to an inlet side of said first two-way valve and an outlet side of said check valve and to said patient treatment station.

4. Apparatus as set forth in claim 1 wherein said third cartridge comprises:
 a) a cylindrical housing having first and second end caps secured to opposite ends of said housing, wherein one end cap includes an inlet port and the other includes an outlet port;
 b) a plurality of porous means mounted within said housing to define a plurality of seriatim chambers, wherein a first chamber defined adjacent the inlet port includes the second bactericide, wherein a second chamber comprises a cavity space, and wherein a third chamber defined adjacent the outlet port includes the third bactericide.

5. Apparatus as set forth in claim 4 wherein said bactericide comprises a multi-valent iodine resin.

6. Apparatus as set forth in claim 5 wherein a plurality of screen members mate with one another to separate each of said second and third bactericides from said cavity space.

7. A water treatment system comprising:
 a) a plurality of manifolds wherein each manifold includes a disposable water treatment cartridge and means for containing each cartridge within each manifold and directing liquid flow through each cartridge, wherein a concentrator one of said cartridges comprises first and second chambers which contain first and second bactericides and which first and second chambers are separated by an intermediate open cavity, and wherein said first and second bactericides provide a concentration of 3 to 10 ppm of bactericide to said liquid;
 b) means for coupling an inlet port of one of said manifolds to a water supply;
 c) means for coupling each of said manifold means in flow communication with one another; and
 d) means for coupling an outlet port of said one of said manifolds in close proximity to a patient treatment station such that said system provides water to said patient treatment station having a bactericide concentration sufficient to maintain distribution conduits intermediate said patient treatment station essentially bacteria and contaminant free.

8. Apparatus as set forth in claim 7 wherein said concentrator cartridge comprises:
 a) a cylindrical housing having first and second end caps secured to opposite ends of said housing, wherein one end cap includes an inlet port and the other includes an outlet port;
 b) a plurality of porous screens mounted within said housing to define a plurality of seriatim chambers, wherein a first chamber defined adjacent the inlet port includes said first bactericide, wherein a second chamber comprises a cavity space and wherein a third chamber defined adjacent the outlet port includes said second bactericide, and wherein at least one of said first and second bactericides comprises a multi-valent iodine resin.

9. Apparatus as set forth in claim 8 wherein said first and second bactericides each comprise a multi-valent iodine resin.

10. Apparatus as set forth in claim 9 wherein said first and second bactericides comprise equal quantities of said multi-valent iodine resin.

* * * * *